US00PP18302P2

(12) United States Plant Patent
Van Zanten

(10) Patent No.: US PP18,302 P2
(45) Date of Patent: Dec. 11, 2007

(54) ***OSTEOSPERMUM* PLANT NAMED 'GG DEL PWN06'**

(50) Latin Name: *Osteospermum ecklonis*
Varietal Denomination: GG DEL PWN06

(75) Inventor: Leo Van Zanten, Oxnard, CA (US)

(73) Assignee: G & G Breeding Corporation, Oxnard, CA (US)

( * ) Notice: Subject to any disclaimer, the term of this patent is extended or adjusted under 35 U.S.C. 154(b) by 0 days.

(21) Appl. No.: 11/394,707

(22) Filed: Mar. 31, 2006

(51) Int. Cl.
*A01H 5/00* (2006.01)

(52) U.S. Cl. ..... Plt./360
(58) Field of Classification Search ..... Plt./360
See application file for complete search history.

*Primary Examiner*—Wendy C. Haas
*Assistant Examiner*—Georgia Helmer

(57) ABSTRACT

A new and distinct *Osteospermum* plant cultivar is disclosed, characterized by daisy type inflorescences, freely flowering under outdoor growing conditions with continuous blooming from spring through autumn, lavender and violet spoon ray florets, and dark blue disc florets.

1 Drawing Sheet

Latin name of the genus and species: *Osteospermum ecklonis.*
Variety denomination: 'GG DEL PWN06'.

BACKGROUND OF THE INVENTION

The new cultivar 'GG DEL PWN06' is a product of open pollination in a heterogeneous population of *Osteospermum* mass selection. The new cultivar was discovered and selected by Leo Van Zanten in May 2004 in Carpinteria, Calif.

Asexual reproduction of the new cultivar 'GG DEL PWN06' by cuttings from adventitious shoots was performed in Oxnard, Calif., and has shown that the unique features of this new cultivar are stable and reproduced true to type on successive generations.

SUMMARY OF THE INVENTION

The cultivar 'GG DEL PWN06' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GG DEL PWN06.' These characteristics in combination distinguish 'GG DEL PWN06' as a new and distinct *Osteospermum* cultivar.

1. Daisy type inflorescence;
2. Lavender and violet spoon-type ray florets;
3. Dark blue disc florets; and
4. A free branching habit.

There is no parent variety to compare to 'GG DEL PWN06'.

In comparison to the commercially available variety 'Aknik' (U.S. Plant Pat. No. 14,316), 'GG DEL PWN06' is smaller in both height and plant spread. Also, 'GG DEL PWN06' has more leaves per lateral branch and obovate-shaped leaves comapred to the elliptical-shaped leaves of the comparable variety. Additionally, 'GG DEL PWN06' has less inflorescences per plant and a wider disc diameter. Finally, the ray florets of the new variety 'GG DEL PWN06' are a different color than the comparable variety, with a much lighter base, more blue-violet than purple at the tubular midsection and more purple at the apex.

BRIEF DESCRIPTION OF THE PHOTOGRAPH

The accompanying photograph in drawing illustrates in full color a typical plant of 'GG DEL PWN06' grown in a 6-inch pot, planted late October and grown outdoors. The plant is 18 weeks old. The growing temperature ranged from 12° C. to 15° C. at night to 12° C. to 20° C. during the day. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'GG DEL PWN06' plants grown in Oxnard, Ventura County, Calif., during the months of October through February. The growing temperature ranged from 12° C. to 15° C. at night to 12° C. to 20° C. during the day. Measurements and numerical values represent averages of typical flowering types.

Botanical classification: *Osteospermum ecklonis* cultivar 'GG DEL PWN06.'
Commercial classification: Garden-type *Osteospermum.*

PROPAGATION

Time to rooting: 10 to 14 days at approximately 21° C.
Root description: Fine, fibrous.

PLANT

Growth habit: Mounding outwardly spreading herbaceous perennial.
Height: Approximately 30 cm.
Plant spread: Approximately 35 cm.
Growth rate: Vigorous.
Branching characteristics: Free Branching.
Length of lateral branches: Approximately 15 cm.
Number of leaves per lateral branch: Approximately 50.
Age of plant described: Approximately 130 days.

FOLIAGE

Leaf:
*Arrangement.*—Alternate single.
*Average length.*—Approximately 5 cm.
*Average width.*—Approximately 1.4 cm.
*Shape of blade.*—Obovate.
*Apex.*—Broadly acuminate.
*Base.*—Attenuate.
*Attachment.*—Stalked.
*Margin.*—Entire with occasional tiny serrations.
*Texture of top surface.*—Lightly pubescent.
*Texture of bottom surface.*—Lightly pubescent.
*Leaf internode length.*—Approximately 2 cm.
*Color.*—Young foliage upper side: Near Green 137A. Young foliage under side: Near Green 137C. Mature foliage upper side: Near Green 137A. Mature foliage under side: Near Green 138A.
*Venation.*—Type: Pinnate. Venation color upper side: Near Yellow-Green 144A. Venation color under side: Near Yellow-Green 144A.

Petiole:
*Average length.*—Approximately 1.6 cm.
*Color.*—Near Yellow-Green 144A.
*Diameter.*—Approximately 0.2 cm.

BLOOM

Inflorescence:
*Flowering habit.*—Freely flowering under outdoor growing conditions with continuous blooming from spring through autumn and year round in a greenhouse environment.
*Inflorescence form.*—Daisy.
*Natural flowering season.*—Continuous throughout February to September in temperature regions.
*Number of inflorescences per lateral branch.*—Approximately 5 open inflorescences.
*Inflorescence diameter.*—Approximately 5.6 cm.
*Inflorescence depth.*—Approximately 1.5 cm.
*Disc diameter.*—Approximately 1.5 cm.
*Inflorescence longevity on plant.*—Approximately 5 to 10 days; longevity of individual flowers are very dependent on temperature and light conditions.
*Persistence.*—Persistent.

Ray florets:
*Appearance.*—Matte.
*Texture.*—Smooth.
*Average number of ray florets per inflorescence.*—23.
*Shape.*—Spoon.
*Aspect.*—Slightly cupped, facing upward or outward.
*Margin.*—Entire.
*Apex.*—Obtuse.
*Length.*—Approximately 3 cm.
*Width.*—Approximately 0.4 cm.
*Color.*—Upper surface at first opening: Lighter than Red-Purple 62D at base; near Violet-Blue 89D at tubular midsection; and near Red-Purple 70B at apex. Upper surface at maturity: Near Red-Purple 62D at base; near Violet-Blue 89D at tubular midsection; and near Purple 78C at apex. Upper surface at fading: Near Red-Purple 62D at base; near Red-Purple 63C at center to near Purple 77C and Purple 77A at extreme tip. Under surface at first opening: Near Violet-Blue 91D with shades of Violet-Blue 89D. Under surface at maturity: Near Violet-Blue 91D with longitudinal stripes of near Blue 103C and Violet 85C to apex. Under surface at fading: Near Violet-Blue 91D with longitudinal stripes of near Blue 103C and Violet 85C to apex.

Disc florets:
*Appearance.*—Matte.
*Texture.*—Smooth.
*Average number of florets per disc.*—Approximately 86.
*Shape.*—Tubular.
*Apex.*—Five-pointed.
*Average length.*—Approximately 0.4 cm.
*Average weight.*—Approximately 0.1 cm.
*Color.*—At first opening: Near Blue 103A. At maturity: Near Blue 103A. At fading: Near Blue 103A.

Peduncle:
*Length.*—Approximately 14 cm.
*Angle.*—Terminal peduncles, erect; secondary and tertiary peduncles, about 45° from vertical.
*Strength.*—Moderate.
*Color.*—Near Yellow-Green 144A with patches of Yellow-Green 148A.
*Habit.*—Upright.
*Diameter.*—Approximately 0.2 cm.
*Surface texture.*—Lightly pubescent.

Inflorescence bud:
*Length.*—Approximately 1.3 cm.
*Diameter.*—Approximately 1.3 cm.
*Form.*—Ovoid to elliptic.
*Color.*—Near Green 137A.

Involucral bracts (phyllaries):
*Appearance.*—Matte.
*Texture.*—Lightly pubescent.
*Number.*—Approximately 24.
*Shape.*—Lanceolate.
*Margin.*—Entire.
*Apex.*—Narrowly acute.
*Length.*—Approximately 1.4 cm.
*Width.*—Approximately 0.2 cm.
*Color.*—Upper side: Near Green 137A. Under side: Near Green 137B.

REPRODUCTIVE ORGANS

*Androecium.*—Present on disc florets only. Number of stamens: 5. Anther shape: Linear. Anther length: Approximately 1.2 mm. Anther color: Near Blue 103A. Amount of pollen: Not abundant. Pollen color: Near Yellow-Orange 15A.
*Gynoecium.*—Present on ray and disc florets. Pistil Number: One. Pistil length: Approximately 5 mm. Stigma shape: Two parted. Stigma length: Approximately 1.1 mm. Stigma color: Near Purple 79A. Style length: Approximately 0.1 cm. Style color: Near Purple 79A.

OTHER CHARACTERISTICS

Disease resistance: Neither resistance nor susceptibility to diseases or pests has been observed in this variety.

Drought tolerance/cold tolerance: Plants are moderately drought tolerant. Plants and cold, less than 12.8° C. for flower induction.

Fruit/seed production: Commercially, this plant is not used or observed in a stage where seeds would be produced. Therefore, seed production has not been observed.

What is claimed is:

1. A new and distinct cultivar of *Osteospermum* plant named 'GG DEL PWN06' as herein illustrated and described.

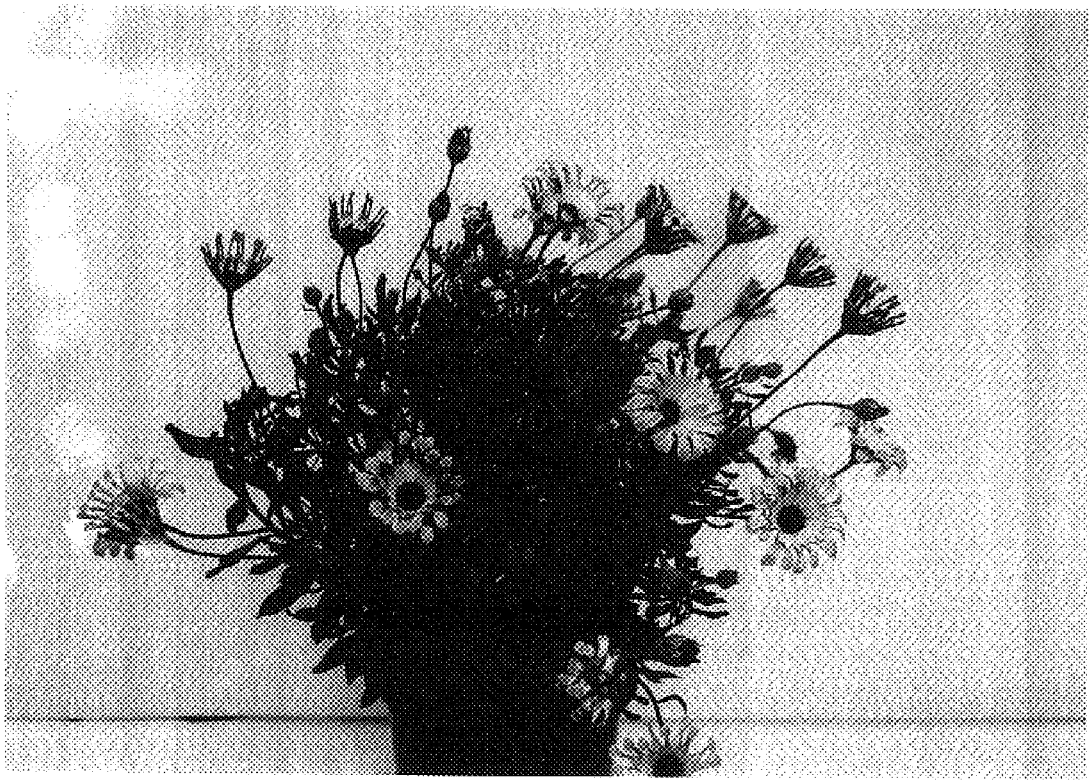

* * * * *